(12) United States Patent
Biedermann et al.

(10) Patent No.: US 9,364,266 B2
(45) Date of Patent: Jun. 14, 2016

(54) RECEIVING PART FOR RECEIVING A ROD FOR COUPLING THE ROD TO A BONE ANCHORING ELEMENT AND A BONE ANCHORING DEVICE WITH SUCH A RECEIVING PART

(71) Applicant: Biedermann Technologies GmbH & Co. KG, Donaueschingen (DE)

(72) Inventors: Lutz Biedermann, VS-Villingen (DE); Timo Biedermann, Trossingen (DE); Berthold Dannecker, St. Georgen (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 426 days.

(21) Appl. No.: 13/905,062

(22) Filed: May 29, 2013

(65) Prior Publication Data

US 2013/0338721 A1    Dec. 19, 2013

Related U.S. Application Data

(60) Provisional application No. 61/652,646, filed on May 29, 2012.

(30) Foreign Application Priority Data

May 29, 2012  (EP) .................................... 12169894

(51) Int. Cl.
*A61B 17/70* (2006.01)
(52) U.S. Cl.
CPC .......... *A61B 17/7049* (2013.01); *A61B 17/7034* (2013.01); *A61B 17/7037* (2013.01)
(58) Field of Classification Search
CPC ........... A61B 17/7049; A61B 17/7034; A61B 17/7037
See application file for complete search history.

(56) References Cited

U.S. PATENT DOCUMENTS 5,672,176 A    9/1997    Biedermann et al.
6,063,090 A    5/2000    Schläpfer
(Continued)

FOREIGN PATENT DOCUMENTS

CN    101357073 A    2/2009
CN    101754725 A    6/2010
(Continued)

OTHER PUBLICATIONS

Extended European Search Report for European Application No. 12169894.8, European Search Report dated Sep. 5, 2012 and mailed Sep. 13, 2012 (7 pgs.).

(Continued)

*Primary Examiner* — Ellen C Hammond
(74) *Attorney, Agent, or Firm* — Lewis Roca Rothgerber Christie LLP (57) ABSTRACT

A receiving part for coupling a rod to a bone anchoring element includes a receiving part body having a first end, a second end, a channel for receiving a rod, an accommodation space for accommodating a head of a bone anchoring element, and an opening at the second end for inserting the head, and a pressure element configured to be positioned at least partly in the accommodation space, the pressure element having a first end, a second end, a central axis, and a flexible portion to clamp an inserted head. The flexible portion has a first slit spaced apart from the second end of the pressure element that extends at least partially around the central axis, and a second slit that extends from the second end of the pressure element into the first slit. The first slit extends away from the second slit and is longer than the second slit.

25 Claims, 8 Drawing Sheets

(56) References Cited

U.S. PATENT DOCUMENTS

| | | | |
|---|---|---|---|
| 8,002,806 B2 * | 8/2011 | Justis | A61B 17/7038 606/246 |
| 8,361,129 B2 * | 1/2013 | Chao | A61B 17/7037 606/264 |
| 8,888,827 B2 * | 11/2014 | Harper | A61B 17/7056 606/266 |
| 8,926,671 B2 * | 1/2015 | Biedermann | 606/268 |
| 8,940,024 B2 * | 1/2015 | Biedermann | A61B 17/7034 606/269 |
| 8,998,959 B2 * | 4/2015 | Jackson | A61B 17/7037 606/267 |
| 9,168,069 B2 * | 10/2015 | Jackson | A61B 17/7037 |
| 2007/0090238 A1 | 4/2007 | Justis | |
| 2008/0015580 A1 | 1/2008 | Chao | |
| 2010/0145394 A1 | 6/2010 | Harvey et al. | |
| 2010/0152787 A1 | 6/2010 | Walsh et al. | |
| 2010/0152949 A1 | 6/2010 | Nunan et al. | |
| 2010/0198272 A1 * | 8/2010 | Keyer | A61B 17/7082 606/302 |
| 2010/0234902 A1 | 9/2010 | Biedermann et al. | |

FOREIGN PATENT DOCUMENTS

| | | |
|---|---|---|
| CN | 101810510 A | 8/2010 |
| CN | 102202589 A | 9/2011 |
| EP | 0 836 835 A2 | 4/1998 |
| EP | 2 283 786 A1 | 2/2011 |
| EP | 2 335 625 A1 | 6/2011 |
| WO | WO 2006/047555 A2 | 5/2006 |
| WO | WO 2007/038350 A2 | 4/2007 |
| WO | WO 2008/118295 A2 | 10/2008 |
| WO | WO 2009/015100 A2 | 1/2009 |

OTHER PUBLICATIONS

Search of the Austrian Patent Office by Serv.ip, "Ihr Partner für Forschung and Innovation Express-Recherche zum Stand der Technik," dated Jul. 11, 2012, 7 pp.

English translation of Chinese Office action for Application No. 201310196306.4, dated Mar. 30, 2016, 10 pages.

* cited by examiner

RECEIVING PART FOR RECEIVING A ROD FOR COUPLING THE ROD TO A BONE ANCHORING ELEMENT AND A BONE ANCHORING DEVICE WITH SUCH A RECEIVING PART

CROSS-REFERENCE TO RELATED APPLICATIONS

The present application claims priority to and the benefit of U.S. Provisional Patent Application Ser. No. 61/652,646, filed May 29, 2012, the contents of which are hereby incorporated by reference in their entirety, and claims priority from European Patent Application EP 12 169 894.8, filed May 29, 2012, the contents of which are hereby incorporated by reference in their entirety.

BACKGROUND

1. Field

The invention relates to a receiving part for receiving a rod for coupling the rod to a bone anchoring element, where the receiving part includes a receiving part body with a channel for receiving the rod and an accommodation space for accommodating a head of the bone anchoring element, and a pressure element with a flexible portion to clamp the head. The flexible portion has a first slit provided in a circumferential direction with respect to a head of the bone anchoring element and a second slit extending from an open end of the pressure element into the first slit, so that a slit ring is integrally formed in the pressure element. Such a receiving part, together with a multitude of different bone anchoring elements, may constitute a modular polyaxial bone anchoring system.

2. Description of Related Art

Various designs of polyaxial bone screws, where a head of a bone anchoring element is clamped from the side to lock an angular position of the bone anchoring element relative to a receiving part, are known.

U.S. Pat. No. 5,672,176 describes a bone screw with a receiving part with a conically shaped seat and a conically shaped pressure element which exerts a pressure onto the head from above and from the side. If the cone angle has a value laying within a specific range self-locking of the pressure element within the receiving part takes place which allows to preliminary lock the head within a receiving part while the rod is still movable in order to allow the adjustment of its position.

U.S. Pat. No. 6,063,090 relates to a device used to connect a longitudinal support to a pedicle screw by an accommodating head having a channel to accommodate the longitudinal support. The pedicle screw and the accommodating head are connected via a conical collet chuck in the accommodating head and by a spherical head on the pedicle screw. The device allows engagement of the pedicle screw in the accommodating head after the pedicle screw has been inserted into the bone.

US 2010/0234902 A1 describes a receiving part for receiving a rod for coupling the rod to a bone anchoring element wherein the receiving part includes a receiving part body and a pressure element arranged therein. The pressure element is movable along a longitudinal axis of the receiving part body from an inserting position insert the head, to a pre-locking position to clamp the head in the receiving part by a pre-stress exerted by the pressure element, to a locking position to lock the head in the receiving part.

SUMMARY

It is an object of embodiments of the invention to provide an improved receiving part for receiving a rod for coupling the rod to a bone anchoring element, and a bone anchoring device with such a receiving part, which has a small number of parts and facilitates improved or easier handling during surgery.

The receiving part according to embodiments of the invention includes a pressure element that has a slit ring at its bottom end. The slit ring is integrally connected to the pressure element, which means the slit ring and the remainder of the pressure element are a monolithic piece. The slit ring can expand in a radial direction to allow for insertion of the head of the bone anchoring element. The force necessary for introducing the head into such a flexible portion of the pressure element is reduced compared to known pressure elements that have only longitudinal or coaxial slits.

Furthermore, a distance the pressure element needs to move in an axial direction until expansion of the slit ring allows for insertion of the head of the bone anchoring element can be reduced. This allows and more easily facilitates an in situ mounting procedure of the receiving part to a bone anchoring element that has already been inserted into a bone.

By means of the elasticity of the slit ring, the head of the bone anchoring element can be clamped by friction between the head and the slit ring. A friction fit between the head of the bone anchoring element and the pressure element allows for a preliminary holding of the bone anchor relative to the receiving part in a desired angular position of the bone anchoring element. This position can be changed by overcoming the friction force, as long as the bone anchoring element is not finally locked with respect to the receiving part.

The receiving part and the bone anchoring element can be easily disassembled using a simple tool.

Furthermore, the polyaxial bone anchoring device according to embodiments of the invention has only a few parts, which reduces the costs for manufacturing and facilitates easier handling. Because the slit ring is integrally formed with the pressure element, it will not get lost. Further, the pressure element can be secured in the receiving part body against falling out.

The polyaxial bone anchoring device that includes the receiving part according to embodiments of the invention allows for a modular system, where various bone anchoring elements and/or different receiving parts may be available and can be assembled, on demand, prior to use.

BRIEF DESCRIPTION OF THE DRAWINGS

Further features and advantages of the invention will become more apparent from the description of various embodiments, using the accompanying drawings. In the drawings.

DETAILED DESCRIPTION

Figures 1, 2:
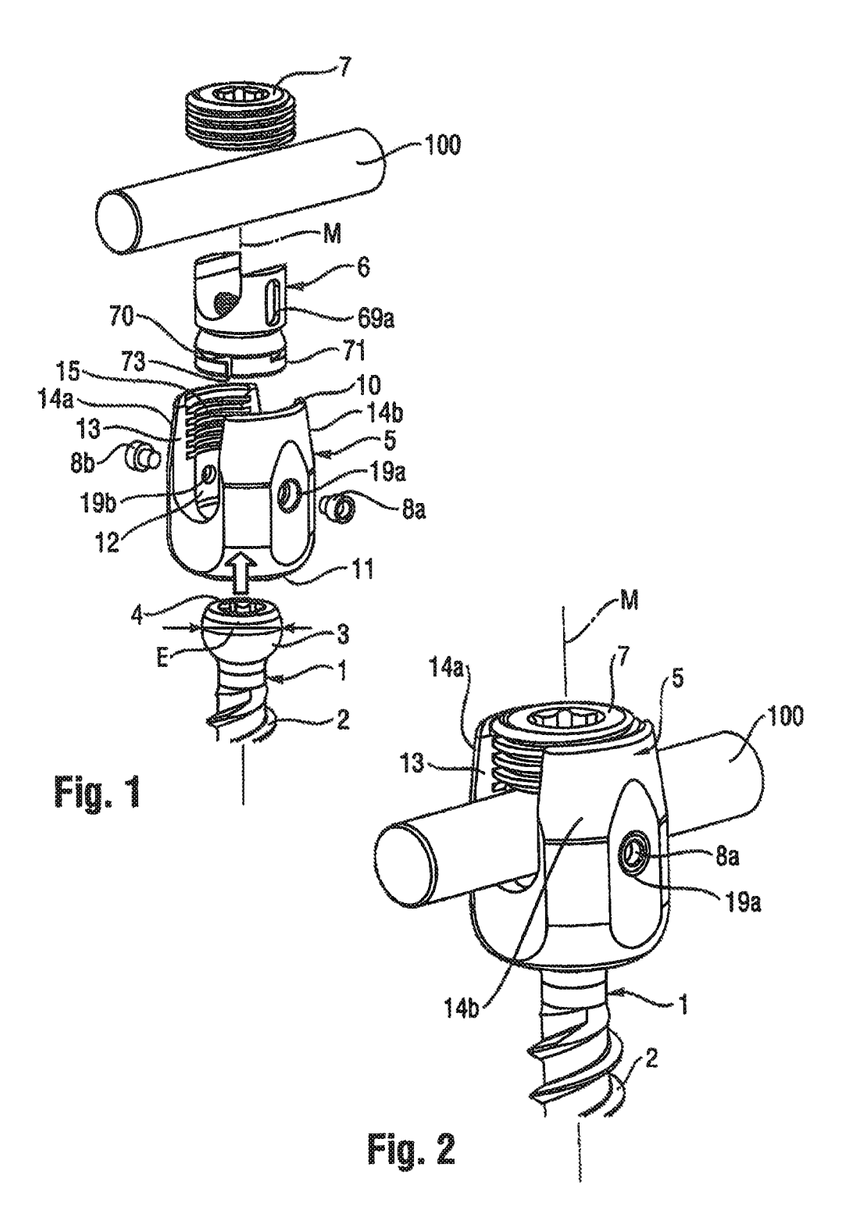
FIG. 1 shows a perspective exploded view of a first embodiment of a bone anchoring device.
FIG. 2 shows a perspective view of the bone anchoring device of FIG. 1 in an assembled state.

As shown in FIGS. 1 and 2, a bone anchoring device according to a first embodiment includes a bone anchoring element 1 in the form of a bone screw having a threaded shaft 2 and a head 3. The head 3 has a spherical segment shaped outer surface portion, including a greatest outer diameter E of the sphere, and a flat free end with a recess 4 for engagement with a screwing-in tool. The bone anchoring device further includes a receiving part for receiving a stabilization rod 100 and for coupling the stabilization rod 100 to the bone anchoring element 1. The receiving part includes a receiving part body 5 and a pressure element 6 configured to be arranged in the receiving part body 5. The pressure element 6 serves for locking the head 3 in the receiving part body 5. Pins 8a, 8b may also be provided for holding the pressure element 6 in the receiving part body 5.

Further, a closure element 7 in the form of an inner screw is provided for securing the rod 100 in the receiving part body 5.

Figure 3:
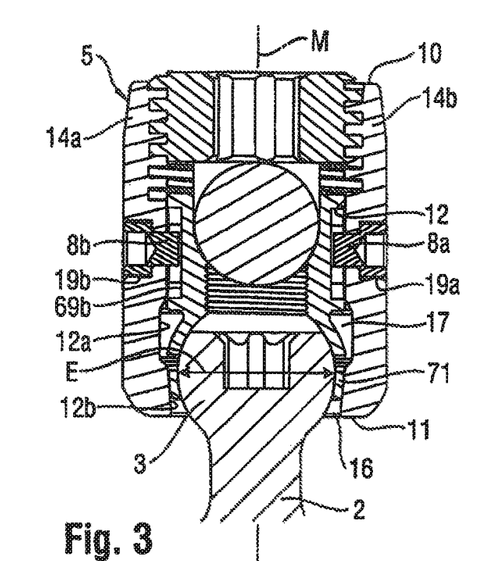
FIG. 3 shows a cross-sectional view of the bone anchoring device according to the first embodiment of FIGS. 1 and 2, the section taken perpendicular to an axis of an inserted rod.
Figure 4:
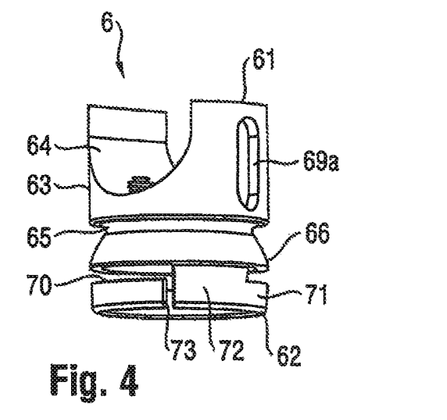
FIG. 4 shows a perspective view of a pressure element according to an embodiment.
Figure 5:
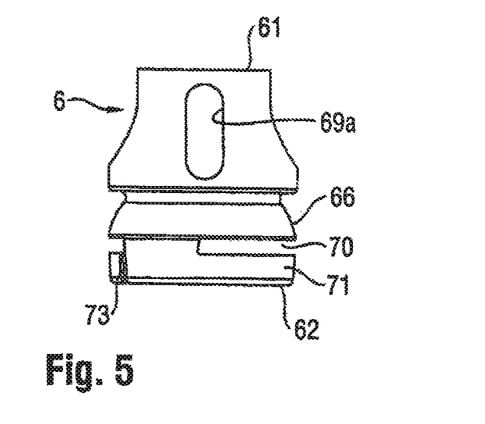
FIG. 5 is a side view of the pressure element of FIG. 4.
Figure 6:
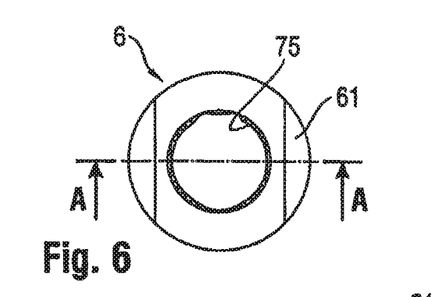
FIG. 6 shows a top view of the pressure element of FIG. 4.

The receiving part body 5 will now be explained with reference to FIGS. 1 to 3. The receiving part body 5 has a top end 10, an opposite bottom end 11, and an axis of symmetry NI passing through the top end 10 and the bottom end 11. A bore 12 is provided that is coaxial to the axis of symmetry M. In a first region adjacent the top end 10, the receiving part body 5 has a U-shaped recess 13 with a bottom directed towards the bottom end 11, and two free lateral legs 14a, 14b extending towards the top end 10. In the region of legs 14a, 14b, an internal thread 15 is provided that cooperates with the inner screw 7. The channel formed by the U-shaped recess 13 is sized so as to receive the rod 100 therein for connecting a plurality of bone anchoring devices. In the region of the legs 14a, 14b, a first portion of the bore 12 has a first inner diameter. In a region below the legs 14a, 14b the bore 12 has a widened portion 12a with a diameter greater than the first inner diameter of the first portion. Between the bottom end 11 and the widened portion 12a, the bore 12 has a narrowing portion 12b that tapers towards the bottom end 11 with a cone angle. An opening 16 is provided at the bottom end 11, the diameter of the opening 16 being larger than the diameter of the head 3 to allow the introduction of the head 3 from the bottom end 11 of the receiving part body 5. The widened portion 12a and the narrowing portion 12b define an accommodation space 17 for the head 3 of the bone anchoring element 1.

On each leg 14a, 14b, bores 19a, 19b are respectively provided, extending through the legs 14a, 14b in a direction substantially perpendicular to the central axis NI for receiving the pins 8a, 8b. The bores 19a, 19b are located approximately at a center of each leg. The pins 8a, 8b preferably have such a length that once inserted into the bores 19a, 19b, the pins 8a, 8b extend a short distance into the bore 12 to provide a stop for the pressure element 6 described below. The pins 8a, 8b may be flush with the outer surface of the receiving part body 5 when inserted.

As can be seen in particular in FIGS. 1 and 4 to 8, the pressure element 6 has a top end 61 and an opposite bottom end 62. Adjacent the top end 61 there is a substantially cylindrical portion 63, which has an outer diameter that is slightly smaller than the inner diameter of the bore 12, so that the pressure element 6 is moveable in the bore 12. There is a U-shaped recess 64 that is open to the top end 61 for receiving the rod 100 therein when the pressure element 6 is arranged in the receiving part body 5, such that the U-shaped recess 64 can be aligned with the U-shaped recess 13 of the receiving part body 5. Adjacent the cylindrical portion 63, a recessed portion 65 is provided that continues into a head receiving portion 66.

The head receiving portion 66 has a hollow interior chamber 67 that is substantially spherical segment shaped and configured to accommodate the head 3 therein. At the bottom end 62, the head receiving portion 66 has an opening to allow the introduction of the head 3. In a region adjacent the recessed portion 65, the head receiving portion 66 has a spherical segment shaped outer surface portion that continues into a tapered outer surface portion in a direction towards the second end 62. The taper corresponds substantially to a taper of the narrowing portion 12b of the receiving part body 5.

At a distance from the bottom end 62, a circumferentially extending slit 70 is provided. The slit 70 extends circumferentially around the central axis M of the receiving part body 5 along a plane substantially perpendicular to the central axis M when the pressure element 6 is arranged in the receiving part body 5. The slit 70 extends around more than 180°, preferably more than 270°, and further preferably more than 340°, around the central axis M. Hence, by means of the slit 70, a ring-shaped portion 71 at the bottom end 62 is provided that is integrally connected to the rest of the pressure element 6 by a wall portion forming a connecting strip 72.

The connecting strip 72 has such a length in a circumferential direction that it provides a stable connection of the ring-shaped portion 1 to the rest of the pressure element 6. At one end of the circumferentially extending slit 70, there is a slit 73 that extends from the second end 62 fully through the ring-shaped portion 71 into the slit 70. By means of this, the ring-shaped portion 71 is cut through or split in a circumferential direction, and forms a slit ring that can be xpanded and compressed in a radial direction. A width of the vertical slit 73 is preferably smaller than the width of the circumferential slit 70. This can be seen in particular in FIGS. 4 and 7. The outer surface of the slit ring 71 is tapered towards the bottom end 62 of the pressure element 6. The connecting strip 72 and the vertical slit 73 are arranged at an angle (i.e., are offset) relative to the U-shaped recess 64. A position and size of the slit ring 71 is such that when the head 3 of the bone anchoring element 1 is inserted from the open bottom end 62 of the pressure element 6, the slit ring 71 expands so that the width of the vertical slit 73 becomes larger, and when the head 3 has been fully inserted into the hollow interior chamber 67, the slit ring 71 encompasses the head 3 at and/or below the greatest diameter E of the head 3 in a direction towards the shaft 2.

A maximum outer diameter of the head receiving portion 66 is slightly smaller than the inner diameter of the first portion of the bore 12 and is also smaller than the diameter of the bore in the widened portion 12a. Hence, the slit ring 71 can expand in the widened portion 12a of the receiving part body 5.

At lateral sides of the U-shaped recess, the pressure element 6 has two elongate recesses 69a, 69b that are elongate in a direction from the top end 61 to the bottom end 62. The recesses 69a, 69b are provided in the outer wall of the pressure element 6. These elongate recesses 69a, 69b serve for engagement by the pins 8a, 8b, respectively, when the pressure element 6 is inserted in the receiving part body 5, and provide for a stop when the pins 8a, 8b abut against one of the ends of the recesses 69a, 69b in an axial direction.

Figure 7:
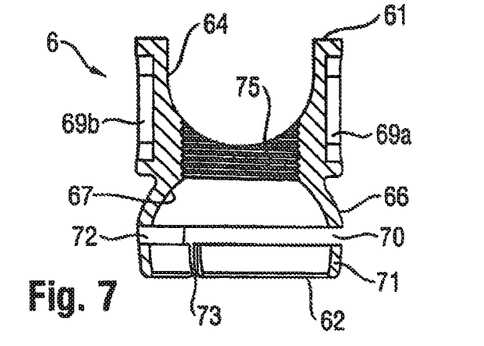
FIG. 7 shows a cross-sectional view of the pressure element of FIGS. 4 to 6, the section taken along line A-A of FIG. 6.
Figure 8:
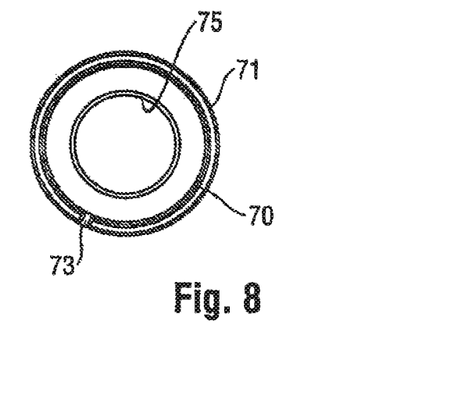
FIG. 8 shows a bottom view of the pressure element of FIG. 4.

Finally, the pressure element 6 has a coaxial through hole 75 allowing access to the recess 4 of the head 3 of the bone anchoring element 1 with a tool (not shown). The through hole 75 is preferably provided with an internal thread in at least a portion thereof, as shown in FIGS. 3 and 7. The internal thread serves for engagement with a tool to fix the pressure element 6 when head 3 of the bone anchoring element 1 is to be removed from the head receiving portion 66, to be described further below.

The pressure element 6 may be arranged in the receiving part body 5 by introduction from the top end 10 of the receiving part body 5, and by aligning the U-shaped recesses 64, 13 of the pressure element 6 and the receiving part body 5, respectively. The pins 8a, 8b may be inserted thereafter to extend into the elongate recesses 69a, 69b of the pressure element 6, to hold the pressure element 6 within the receiving part body 5, thereby preventing escaping of the pressure element 6 through the first end 10. By means of this, the pressure element 6 and the receiving part body 5 can be pre-assembled and can be connected to a bone anchoring element 1.

All the parts described above may be made of a bio-compatible material, such as a bio-compatible metal like stainless steel or titanium, or of a bio-compatible metal alloy, such as Nitinol, or of a bio-compatible plastic material, for example, Polyetheretherketon (PEEK). The parts may all be made of the same material or of different materials.

Figure 9:
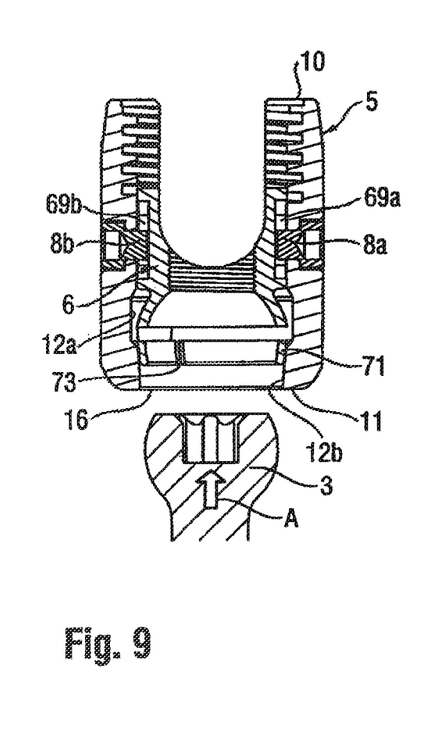
FIGS. 9 to 14 show steps of assembling a bone anchoring element and a receiving part of the bone anchoring device according to the first embodiment.
Figure 10:
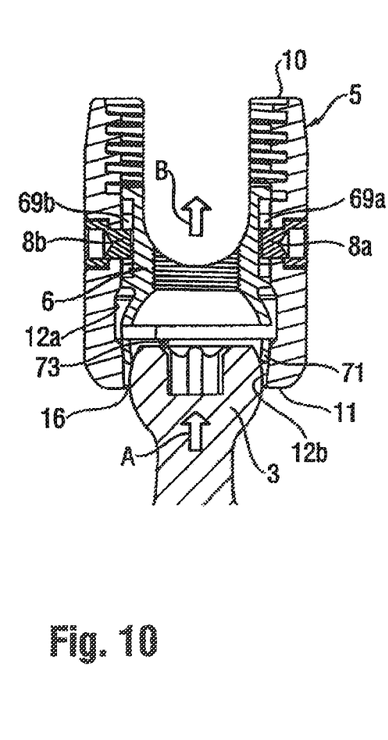
Figure 11:
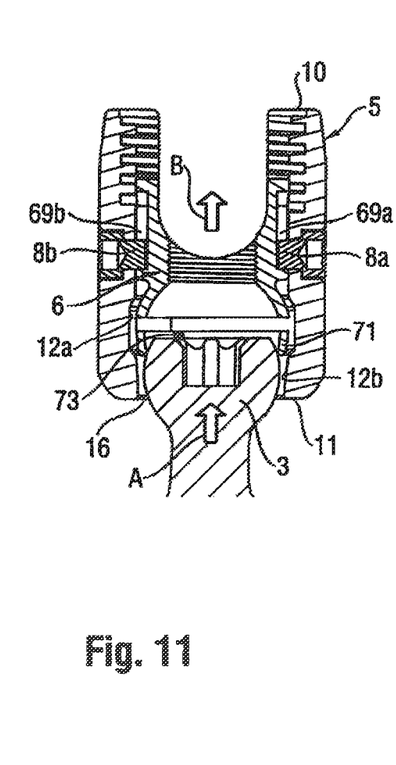
Figure 12:
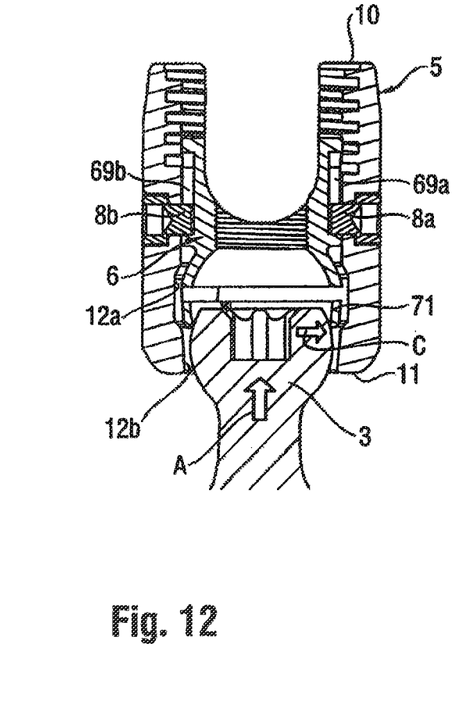

Steps of assembling the bone anchoring device will now be explained with reference to FIGS. 9 to 14. As shown in FIG. 9, the pressure element 6 and the receiving part body 5 can be pre-assembled as described above. The slit ring 71 may abut against the upper part of the narrowing portion 12b. The bone anchoring element 1 is introduced from the bottom end 11 of the receiving part body 5 (arrow A). Next, as shown in FIG. 10, the head 3 of the bone anchoring element is introduced from the bottom end 11 and touches the slit ring 71 of the pressure element 6, thereby shifting the pressure element 6 in a direction of the arrow B, until a lower end of the elongate recesses 69a, 69b abut against the pins 8a, 8b, respectively, as shown in FIG. 11. In this position, the slit ring 71 is situated in the accommodation space provided by the widened portion 12a of the receiving part body 5.

Figure 13:
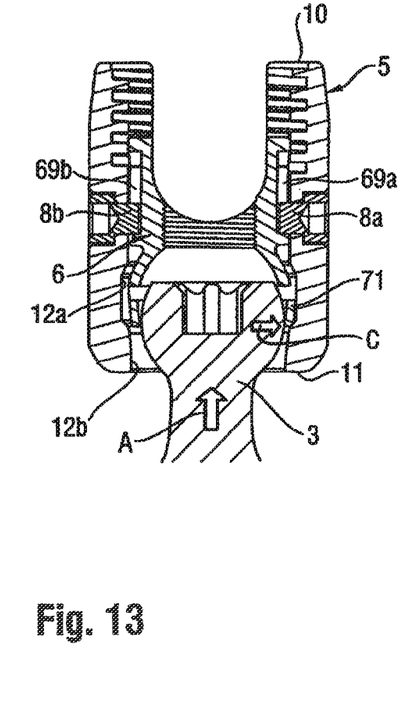
Figure 14:
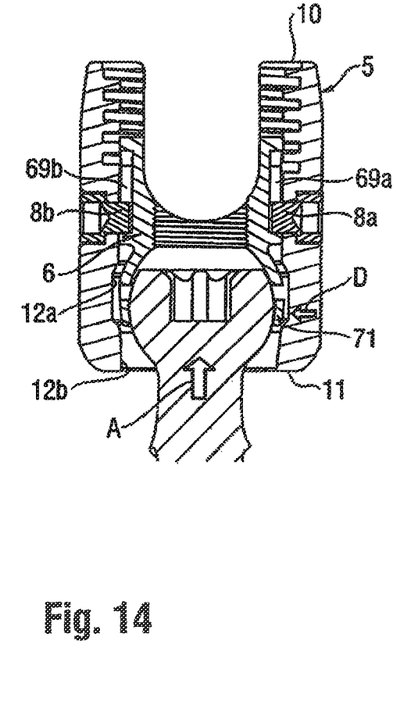

Further introduction of the head 3 into the head receiving portion 66 expands the slit ring 71 within the widened portion 12a of the receiving part body 5. The head 3 can then be inserted. Because the slit ring 71 does not expand at the connecting strip 72, the introduction of the head 3 may not be precisely coaxial with to the axis of symmetry M, but instead may be slightly out of or misaligned with the axis of symmetry M. By the further introduction of the head 3, the slit ring 71 may be expanded to a maximum extent, as shown in FIG. 13. Still further introduction of the head 3 allows the head 3 to enter the upper space or portion of the hollow interior chamber 67, until the head 3 abuts against the inner wall of the chamber 67. Here, the slit ring 71 can elastically contract around the head 3, as shown in FIG. 14.

Figure 15:
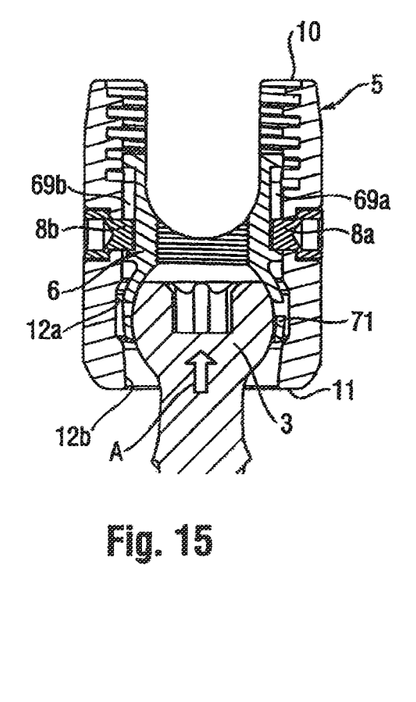
FIGS. 15 and 16 show two positions of the pressure element in the receiving part with inserted bone anchoring element according to the first embodiment.

When the head 3 abuts against the inner wall of the head receiving portion 66 in the upper region, the slit ring 71 encompasses a portion of the head 3 below the equator E as can be seen in FIG. 15. In this condition, the slit ring 71 frictionally clamps the head 3, so that the bone anchoring element 1 can be pivoted to a desired angular position relative to the receiving part body 5, and can be held there by the friction fit between the pressure element 6 and the head 3.

Figure 16:
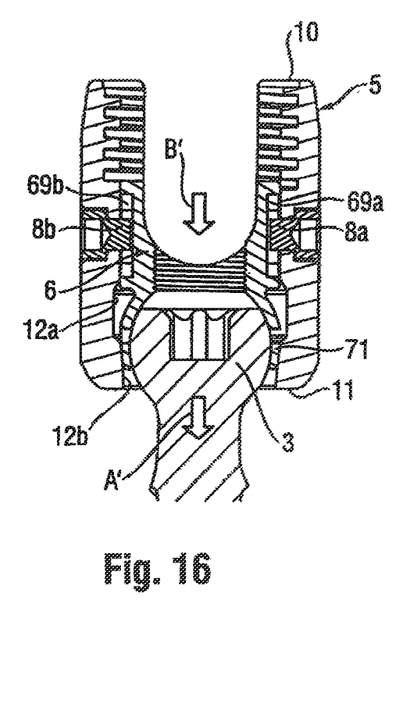

Finally, moving down the pressure element 6 presses the slit ring 71 into the narrowing portion 12b, so that the slit ring 71 locks the head 3, as shown in FIG. 16.

In clinical use, first the receiving part may be assembled with the bone anchoring element 1 as described above, then the bone anchoring element 1 may be inserted into a bone. Usually at least two bone anchoring devices are inserted into the bone and the receiving parts are aligned. Then, the rod 100 is inserted into the respective receiving parts. Finally, the inner screws 7 are screwed between the legs 14a, 14b of the devices, and the rod 100 presses down on the respective pressure elements so that the respective heads 3 are locked therein.

Alternatively, the bone anchoring element 1 can first be inserted into a bone, and the receiving part body 5 with the pressure element 6 can be mounted thereafter onto the head 3 of the bone anchoring element 1. Because of the slit ring 71, the force necessary to insert the head 3 into the head receiving portion 66 of the pressure element 6 can be reduced, and a distance needed to move the pressure element 6 within the bore 12 of the receiving part body 5 can also be reduced.

Figure 17:
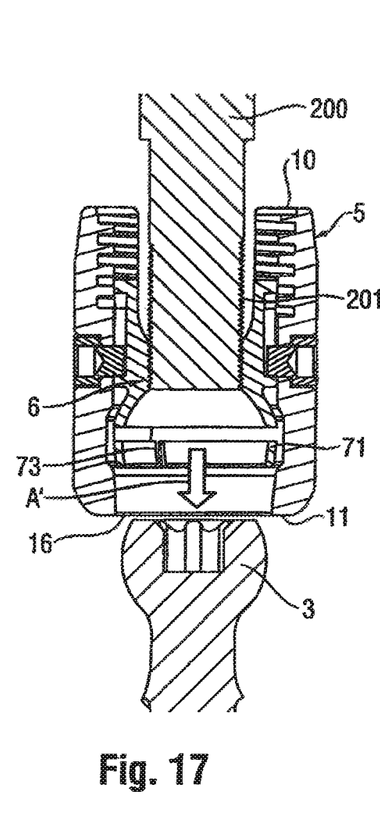
FIG. 17 shows a step of disassembling the receiving part and the bone anchoring element according to the first embodiment using a tool.

In the case that the receiving part body 5 and the head 3 are to be disassembled, for example, when it may be desirable for the head 3 to be removed from the receiving part body 5, a tool 200 may be used as shown in FIG. 17. The tool 200 may have a first portion to be gripped by a person (not shown) and a threaded end portion 201 that engages the threaded through hole 75 of the pressure element 6. By means of this, the pressure element 6 can be pulled in the direction of the top end 10 of the receiving part body 5 until the pins 8a, 8b abut against the lower end of the elongate recesses 69a, 69b. In this position, the slit ring 71 is located within the accommodation space in the widened portion 12a of the receiving part body 5. Then, the head 3 can be removed through the bottom end 11 of the receiving part body 5.

Figure 18:
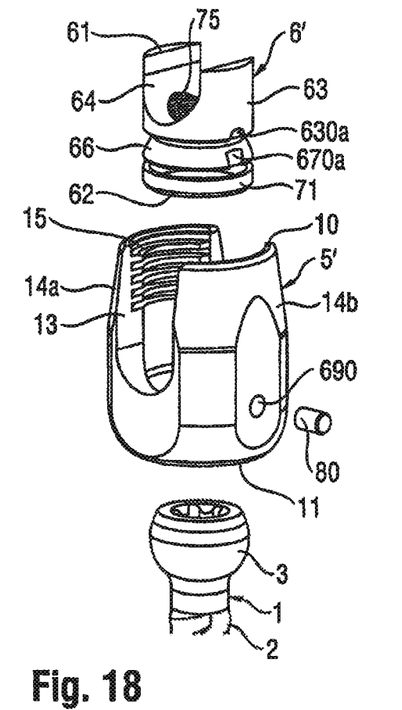
FIG. 18 shows a perspective exploded view of a bone anchoring device according to a second embodiment.
Figure 19:
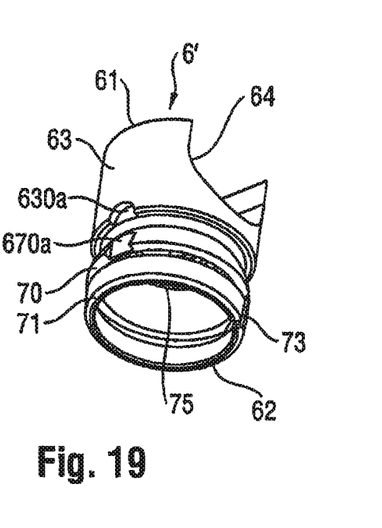
FIG. 19 shows a perspective view of a pressure element of the bone anchoring device according to the second embodiment.
Figure 20:
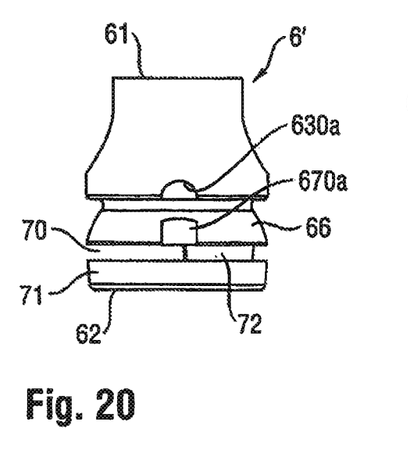
FIG. 20 shows a side view of the pressure element according to the second embodiment.
Figure 21:
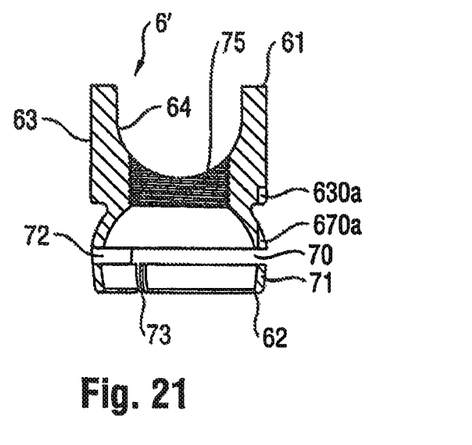
FIG. 21 shows a cross-sectional view of the pressure element of FIG. 19.
Figure 22:
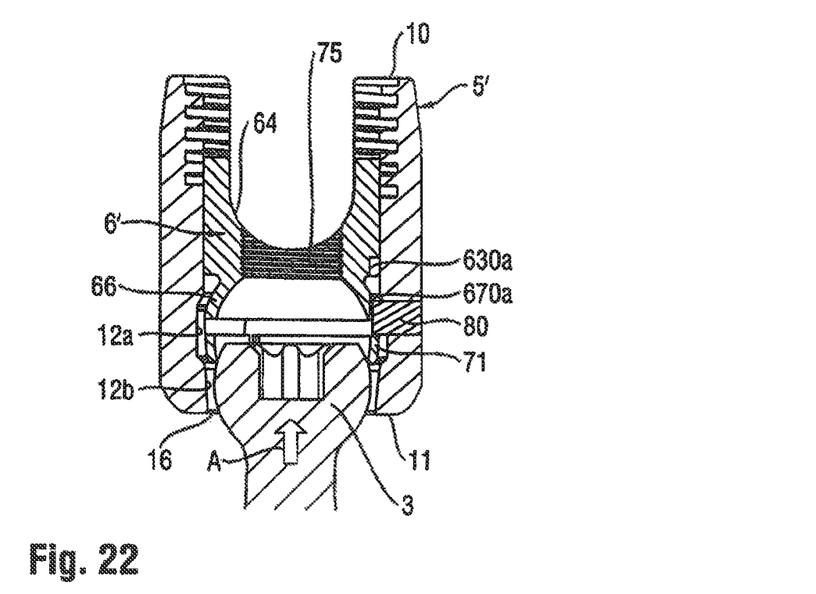
FIGS. 22 and 23 show steps of assembling and locking the bone anchoring device according to the second embodiment.
Figure 23:
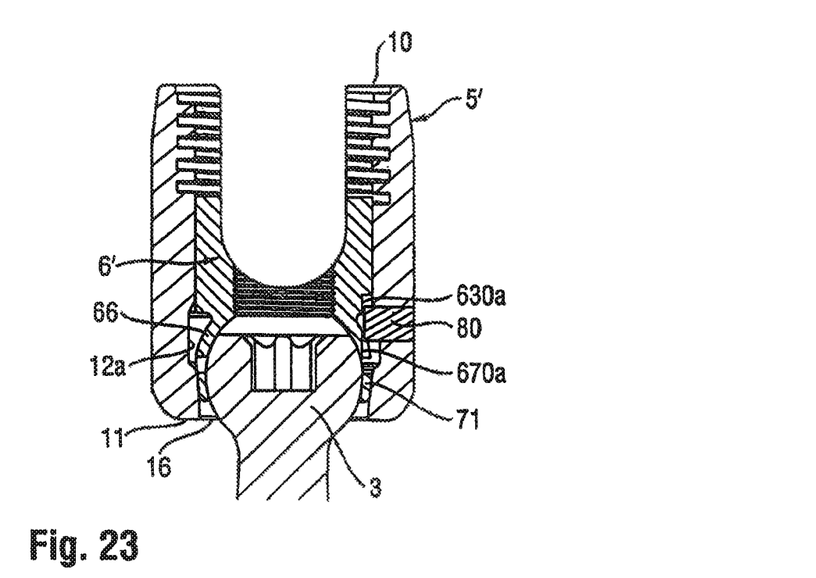
Figure 24:
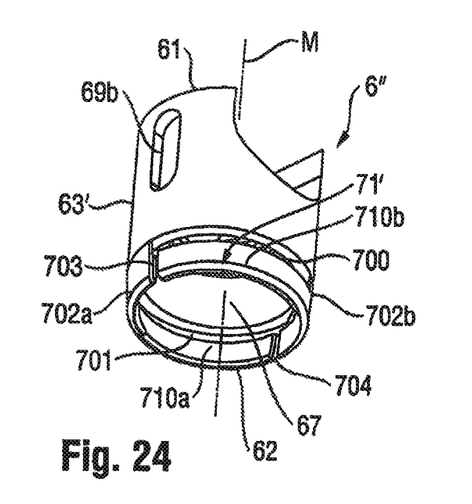
FIG. 24 shows a perspective view of a further embodiment of a pressure element of the bone anchoring device.
Figure 25:
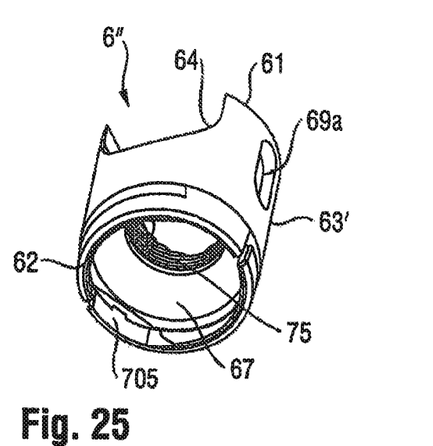
FIG. 25 shows the pressure element of FIG. 24 from a bottom perspective view.
Figure 26:
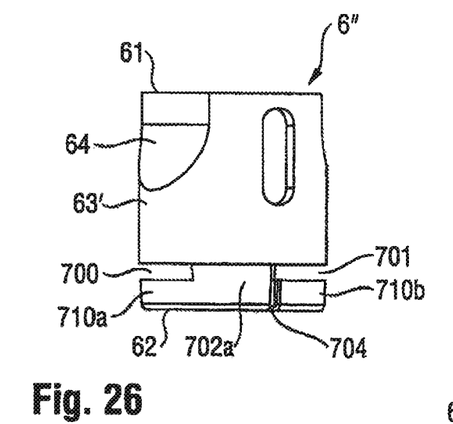
FIG. 26 shows a side view of the pressure element of FIG. 24.
Figure 27:
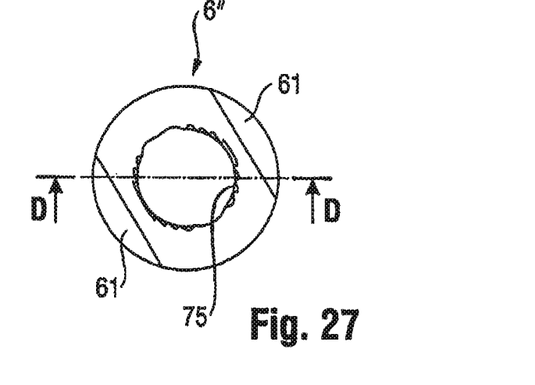
FIG. 27 shows a top view of the pressure element of FIG. 24.
Figure 28:
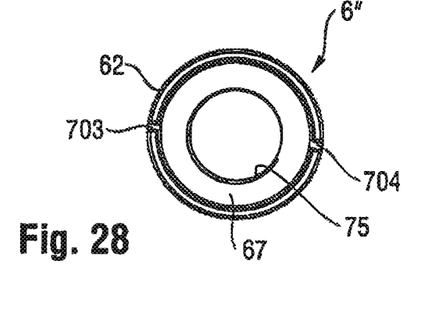
FIG. 28 shows a bottom view of the pressure element of FIG. 24.
Figure 29:
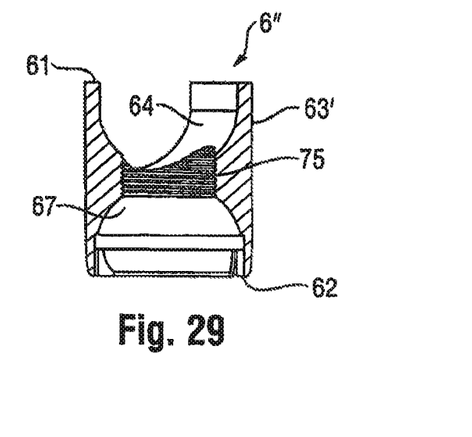
FIG. 29 shows a cross-sectional view of the pressure element of FIGS. 24 to 27, the section taken along line D-D shown in FIG. 27.

A second embodiment of the bone anchoring device is shown in FIGS. 18 to 23. With reference to FIG. 18, the bone anchoring device according to the second embodiment differs from the bone anchoring device according to the first embodiment in that the receiving part body 5' has only one lateral bore 690 provided in the leg 14b, at a distance below the bottom of the U-shaped recess 13. Hence, as shown in FIGS. 22 and 23, a single pin 80 extends through the bore 690 into the widened portion 12a of the bore 12. All other parts of the receiving part body 5' are identical or similar to the first embodiment, and the descriptions thereof will not be repeated.

The pressure element 6' has at an end of the cylindrical portion 63 a first substantially semi-circular notch 630a that is open towards the bottom end 62 and is configured to engage with the pin 80 as shown in FIG. 23. Hence, the notch 630a may be provided at a 90° offset to the U-shaped recess 64.

The pressure element 6' further has a second notch 670a that is provided in an axial direction below the first notch 630a in an upper part of the head receiving portion 66. The width of the second notch 670a is slightly larger than the diameter of the pin 80, so that the pin 80 can engage the second notch 670a. As can be seen in particular in FIG. 21, the second notch 670a has such a depth that it is recessed with respect to an outer surface of the slit ring 71. The notches 630a, 670a may be arranged on an opposite side of the connection strip 72, as best seen in FIGS. 20 and 21.

In use, the pressure element 6' and the receiving part body 5' can be pre-assembled. The head 3 is introduced like in the first embodiment from the bottom end 11. When the head 3 is introduced and abuts against the bottom end of the pressure element 6', the slit ring 71 abuts against the pin 80 as shown in FIG. 22. Therefore, the pin 80 provides a stop for the slit ring 71 and prevents bending of the slit ring 71 in a direction towards the top end 10 of the receiving part body 5. Simultaneously, the pin 80 acts as a securing device against escaping of the pressure element 6' and as a positioning device for a correct alignment of the pressure element 6' with respect to the receiving part body 5'.

A further embodiment of the pressure element 6" will be described with reference to FIGS. 24 to 29. The pressure element 6" has, as in the previous embodiments, a top end 61 and a bottom end 62. Adjacent the top end 61, a substantially cylindrical portion 63' is provided that extends to a distance from the bottom end 62, and has, adjacent the top end 61, the U-shaped recess 64. A central bore 75 with a threaded portion is present as in the previous embodiments.

At a distance from the bottom end 62, two slits 700, 701 are provided that extend in a circumferential direction around a central axis M along a plane transverse to the central axis M. At the end of each of the horizontal slits 700, 701, vertical slits 703, 704 are respectively provided, where the vertical slits 703, 704 are located around a circumference of the pressure element 6" at opposite places. The vertical slits 703, 704 extend from the bottom end 62 frilly into the horizontal slits 700, 701, respectively. Hence, two ring portions 710a, 710b that are opposite to each form the flexible section of the pressure element 6". The ring portions 710a, 710b are connected with the cylindrical portion 63 via connecting strips 702a, 702b located opposite to each other. By means of the two ring portions 710a, 710b, a slit ring 71' is formed. The slit ring 71' can expand when the vertical slits 703, 704 are enlarged, and can elastically return to a non-expanded condition.

Because the pressure element 6" is almost not flexible in the region of the connecting strips 702a, 702b, a recess 705 may be provided on one or both of the inner wall portions of the connecting strips 702a, 702b, such that an inner diameter of the pressure element 6" in the region of the connecting strips 702a, 702b is the same or is slightly larger than the largest outer diameter E of the head 3.

Further, the pressure element 6" has an interior chamber 67 with a preferably spherical segment shaped section to accommodate the head 3.

The pressure element 63' can be combined with a receiving part body 5 or 5' according to the first or second embodiments. In addition, the various other features of the embodiments can be combined among each other. The pressure element can be further modified, for example, such that more than two horizontal and/or more than two vertical slits may be provided.

Further modifications of the embodiments shown are also possible. For example, the circumferential slits 70, 700, 701 need not be perpendicular or level relative to the central axis M, but can instead be inclined. The vertical slits 73, 703, 704 can also be inclined or can have a particular contour, as long as the slits extends fully through the respective rings. The head of the bone anchoring element can also have various other shapes, for example, a cylindrical shape where a monoaxial bone screw is provided, allowing for rotation of the bone anchoring element with respect to the receiving part around a single axis. The head can also be, for example, conically shaped. In such embodiments, the hollow interior chamber would then be adapted to correspond to the shape of the head. In a further modification, the receiving part body can have an inclined bottom end to allow for greater angulation of the bone anchoring element in one direction.

In another modification, the narrowing portion of the receiving part body and/or the corresponding outer surface portion of the slit ring may not be tapered, but may instead be spherically curved.

For the bone anchoring element, various different kinds of bone anchoring elements can be used, such as screws of different lengths, of different diameters, of different thread forms, nails with barbs or without barbs, cannulated screws or nails, or hooks among others.

In addition, for the closure element, various known kinds of closure elements can also be used, for example, single part closure elements or double part closure elements, among others.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A receiving part for receiving a rod for coupling the rod to a bone anchoring element, the receiving part comprising:
   a receiving part body having a first end, a second end, a length that extends between the first end and the second end, a channel for receiving the rod, and an accommodation space for accommodating a head of the bone anchoring element, the accommodation space having an opening at the second end for inserting the head; and
   a pressure element configured to be positioned at least partly in the accommodation space, the pressure element having a first end, a second end configured to be positioned closer than the first end of the pressure element to the second end of the receiving part body, a central axis extending through the first and second ends of the pressure element, and a flexible portion to clamp the inserted head of the bone anchoring element, wherein the pressure element has a length that is shorter than the length of the receiving part body;
   wherein the flexible portion has a first slit spaced apart from the second end of the pressure element that extends at least partially around the central axis, and a second slit that extends from the second end of the pressure element into the first slit, and wherein the first slit extends away from the second slit and is longer than the second slit.

2. The receiving part of claim 1, wherein the first slit and the second slit define a slit ring.

3. The receiving part of claim 2, wherein the slit ring is configured to laterally encompass the inserted head of the bone anchoring element, and is connected to other portions of the pressure element in a monolithic manner via at least one connecting strip.

4. The receiving part of claim 2, wherein the slit ring has a tapered exterior surface portion that tapers towards the second end of the pressure element.

5. The receiving part of claim 1, wherein the second slit extends in a direction substantially parallel to the central axis.

6. The receiving part of claim 1, wherein the first slit extends circumferentially in a direction substantially perpendicular to the central axis.

7. The receiving part of claim 1, wherein only a single first slit and only a single second slit are provided on the pressure element.

8. The receiving part of claim 1, wherein two first slits and two second slits are provided on the pressure element.

9. The receiving part of claim 1, wherein the second slit is arranged at one end of the first slit in a circumferential direction.

10. The receiving part of claim 1, wherein the flexible portion has a hollow spherical-segment shaped inner surface portion configured to accommodate the head of the bone anchoring element.

11. The receiving part of claim 1, wherein the first end of the pressure element has a substantially cylindrical portion with a recess that is configured to accommodate the rod.

12. The receiving part of claim 1, further comprising a stop configured to prevent movement of the pressure element towards the first end of the receiving part body when the pressure element is in the receiving part body.

13. The receiving part of claim 1, wherein the pressure element can assume an insertion position in the receiving part body wherein the flexible portion is laterally expandable in the accommodation space, so as to allow introduction of the head of the bone anchoring element through the opening at the second end of the receiving part body into the pressure element.

14. The receiving part of claim 1, wherein the accommodation space is substantially cylindrical, and has a tapered or curved narrowing portion near the second end of the pressure element.

15. The receiving part of claim 14, wherein an outer wall of the pressure element has a tapered or rounded narrowing portion configured to cooperate with the narrowing portion of the accommodation space.

16. A bone anchoring device comprising:
a bone anchoring element having a shaft for anchoring to a bone and a head; and
a receiving part for receiving a rod for coupling the rod to the bone anchoring element, the receiving part comprising:
a receiving part body having a first end, a second end, a length that extends between the first end and the second end, a channel for receiving the rod, and an accommodation space for accommodating the head, the accommodation space having an opening at the second end for inserting the head; and
a pressure element configured to be positioned at least partly in the accommodation space, the pressure element having a first end, a second end configured to be positioned closer than the first end of the pressure element to the second end of the receiving part body, a central axis extending through the first and second ends of the pressure element, and a flexible portion to clamp the head, wherein the pressure element has a length that is shorter than the length of the receiving part body;
wherein the flexible portion has a first slit spaced apart from the second end of the pressure element that extends at least partially around the central axis, and a second slit that extends from the second end of the pressure element into the first slit, and wherein the first slit extends away from the second slit and is longer than the second slit.

17. The bone anchoring device of claim 16, wherein the head has a spherical-segment shaped outer surface portion.

18. The bone anchoring device of claim 16, wherein the flexible portion is sized relative to the head, such that the head is clamped by friction when the head is held in the flexible portion.

19. The bone anchoring device of claim 16, further comprising a closure element for securing the rod in the receiving part body.

20. The bone anchoring device of claim 16, wherein when the head is inserted in the receiving part body and the flexible portion of the pressure element is spaced apart from an inner wall of the receiving part body, the bone anchoring device can assume a position wherein the head is prevented from removal from the receiving part body.

21. A method for coupling a rod to a bone via a bone anchoring device, the bone anchoring device comprising a bone anchoring element having a shaft for anchoring to a bone and a head, a receiving part comprising a receiving part body having a first end, a second end, a length that extends between the first end and the second end, a channel for receiving the rod, and an accommodation space for accommodating the head, the accommodation space having an opening at the second end for inserting the head, and a pressure element configured to be positioned at least partly in the accommodation space, the pressure element having a first end, a second end configured to be positioned closer than the first end of the pressure element to the second end of the receiving part body, a central axis extending through the first and second ends of the pressure element, and a flexible portion to clamp the head, wherein the pressure element has a length that is shorter than the length of the receiving part body, and wherein the flexible portion has a first slit spaced apart from the second end of the pressure element that extends at least partially around the central axis, and a second slit that extends from the second end of the pressure element into the first slit, and wherein the first slit extends away from the second slit and is longer than the second slit, the method comprising:
inserting the bone anchoring element into a bone;
adjusting an angular position of the bone anchoring element relative to the receiving part body;
inserting the rod into the channel of the receiving part body; and
advancing a closure element in the receiving part body to advance the rod and the pressure element away from the first end of the receiving part body, to lock the angular position of the bone anchoring element and a position of the rod relative to the receiving part body.

22. The method of claim 21, further comprising connecting the bone anchoring element with the receiving part body prior to inserting the bone anchoring element into the bone.

23. The method of claim 21, further comprising connecting the bone anchoring element with the receiving part body after inserting the bone anchoring element into the bone.

24. The method of claim 21, further comprising inserting the pressure element into the receiving part body.

25. A receiving part for receiving a rod for coupling the rod to a bone anchoring element, the receiving part comprising:
- a receiving part body having a first end, a second end, a length that extends between the first end and the second end, a channel for receiving the rod, and an accommodation space for accommodating a head of the bone anchoring element, the accommodation space having an opening at the second end for inserting the head; and
- a pressure element configured to be positioned at least partly in the accommodation space, the pressure element having a first end, a second end configured to be positioned closer than the first end of the pressure element to the second end of the receiving part body, a central axis extending through the first and second ends of the pressure element, and a flexible portion to clamp the inserted head of the bone anchoring element, wherein the pressure element has a length that is shorter than the length of the receiving part body;
- wherein the flexible portion has a slit that extends at least partially around the central axis to form a portion at the second end spaced apart from other portions of the pressure element in an axial direction by the slit, and wherein a distance the slit extends around the central axis is greater than a greatest height of the portion at the second end along the axial direction.

* * * * *